(12) United States Patent
Brajnovic

(10) Patent No.: US 8,303,303 B2
(45) Date of Patent: Nov. 6, 2012

(54) DEVICE FOR DETERMINING POSITION

(75) Inventor: Izidor Brajnovic, Göteborg (SE)

(73) Assignee: Nobel BioCare Services AG, Zürich-Flughafen (CH)

( * ) Notice: Subject to any disclaimer, the term of this patent is extended or adjusted under 35 U.S.C. 154(b) by 0 days.

(21) Appl. No.: 12/249,376

(22) Filed: Oct. 10, 2008

(65) Prior Publication Data

US 2009/0123887 A1 May 14, 2009

Related U.S. Application Data

(63) Continuation of application No. 10/451,530, filed as application No. PCT/SE01/02900 on Dec. 27, 2001, now Pat. No. 7,435,088.

(30) Foreign Application Priority Data

Dec. 29, 2000 (SE) ...................... 0004886

(51) Int. Cl.
  *A61C 3/00*   (2006.01)
  *A61C 19/04*  (2006.01)
  *A61C 8/00*   (2006.01)
(52) U.S. Cl. ............................. 433/75; 433/72; 433/173
(58) Field of Classification Search .................. 433/169, 433/172–178, 201.1, 72–75, 215, 218; 411/54.1, 411/56, 57.1, 63, 44, 53, 55, 60.2, 62; 623/17.17; 606/63, 68, 300, 301, 304, 305, 308, 313, 606/314, 319, 320, 323, 326, 327, 329, 80, 606/96

See application file for complete search history.

(56) References Cited

U.S. PATENT DOCUMENTS

| | | | | |
|---|---|---|---|---|
| 2,887,694 A * | 5/1959 | Sauter | | 470/30 |
| 4,756,689 A * | 7/1988 | Lundgren et al. | | 433/173 |
| 4,872,839 A * | 10/1989 | Brajnovic | | 433/173 |
| 4,906,420 A | 3/1990 | Brajnovic et al. | | |
| 4,931,016 A | 6/1990 | Sillard | | |
| 4,986,753 A * | 1/1991 | Sellers | | 433/172 |
| 4,988,297 A | 1/1991 | Lazzara et al. | | |
| 5,040,982 A * | 8/1991 | Stefan-Dogar | | 433/169 |

(Continued)

FOREIGN PATENT DOCUMENTS

EP 0689804 A 1/1936

(Continued)

OTHER PUBLICATIONS

International search report—Apr. 11, 2002.

(Continued)

*Primary Examiner* — Yogesh Patel
(74) *Attorney, Agent, or Firm* — Venable LLP

(57) ABSTRACT

An arrangement for determining position and fixation of an element relative to a part in or on a bone or a model of a bone. An expansion spacer extends through a sleeve. The spacer includes a first flange engages a first end of the sleeve and a second flange engages a second end of the sleeve when the spacer is expanded to vertically fix the spacer relative to the sleeve. An expansion screw extends through the spacer and includes an outer conical expansion surface configured to cooperate with an inner conical expansion surface on the spacer to radially expand the spacer causing the outer surface on the spacer to engage the inner surface of the sleeve, thereby determining the position of the sleeve relative to the part and fixing the sleeve.

30 Claims, 2 Drawing Sheets

U.S. PATENT DOCUMENTS

| | | | |
|---|---|---|---|
| 5,320,529 | A | 6/1994 | Pompa |
| 5,527,182 | A | 6/1996 | Willoughby |
| 5,725,376 | A | 3/1998 | Poirier |
| 5,842,859 | A | 12/1998 | Palacci |
| 5,876,204 | A | 3/1999 | Day et al. |
| 6,197,410 | B1 | 3/2001 | Vallittu et al. |
| 6,227,859 | B1 * | 5/2001 | Sutter ............... 433/173 |
| 6,319,000 | B1 | 11/2001 | Branemark |
| 2004/0013998 | A1 | 1/2004 | Jung et al. |
| 2004/0197729 | A1 | 10/2004 | Honstein et al. |

FOREIGN PATENT DOCUMENTS

| | | |
|---|---|---|
| JP | 7208422 A | 8/1995 |
| JP | 10274218 A | 10/1998 |
| SE | 457691 A | 1/1989 |

OTHER PUBLICATIONS

International preliminary examination report—Mar. 27, 2003.

* cited by examiner

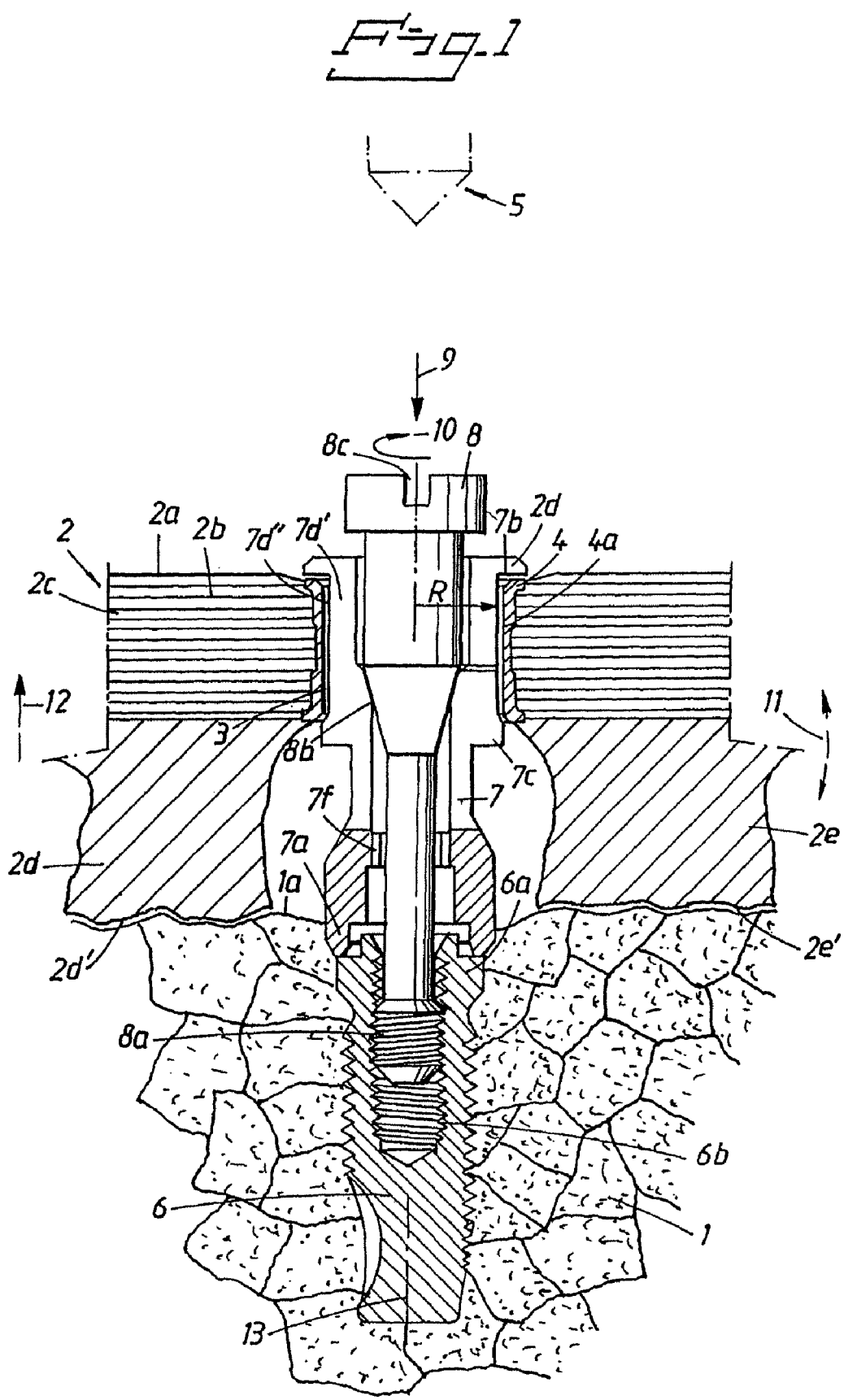

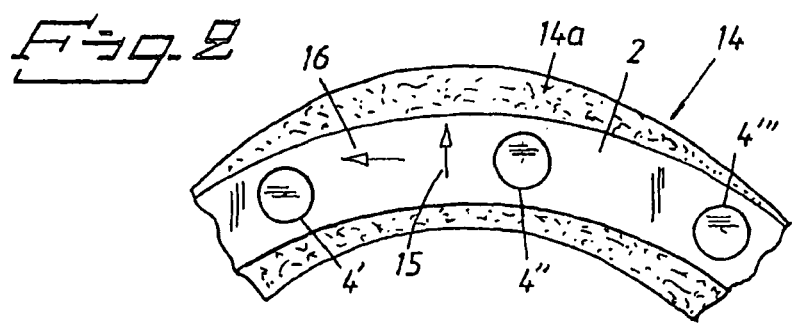
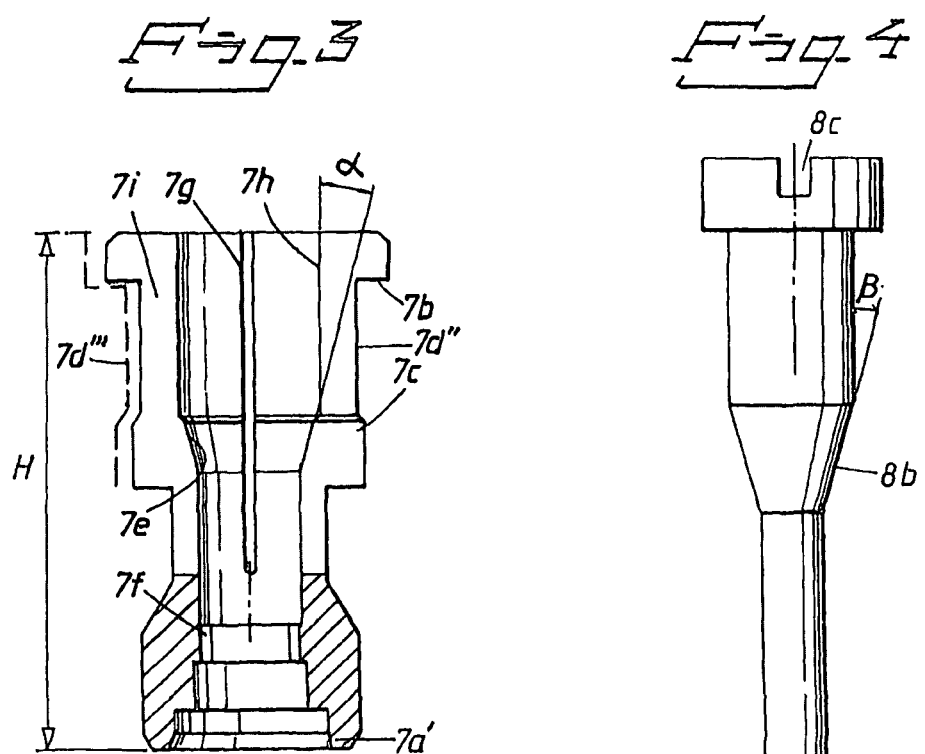

DEVICE FOR DETERMINING POSITION

CROSS-REFERENCE TO RELATED APPLICATIONS

This application is a continuation of U.S. patent application Ser. No. 10/451,530 filed Jun. 24, 2003 now U.S. Pat. No. 7,435,088, which claims priority to Swedish patent application 0004886-8 filed 29 Dec. 2001 and is the national phase under 35 U.S.C.§371 of PCT/SE01/02900 filed Dec 27, 2001.

FIELD OF THE INVENTION

The present invention relates to a device for determining the position of an element, for example a sleeve, on the one hand in the vertical direction in relation to an anchoring part or structural part, for example a fixture or fixture dummy, in or on a bone, for example a jaw bone, or a model of a bone, and on the other hand in the transverse direction in relation to the longitudinal axis of the part.

The invention is intended, inter alia, to be used in connection with the production and the use of assembly templates which are used for hole-forming elements (drill/drills, attachments, etc.) in the jaw bone. The assembly template can be used in connection with a model of the jaw bone and/or in connection with the patient's jaw bone. The invention can be more specifically used on templates or assembly templates which are made of carbon fibre-reinforced plastic, where the assembly template material has a certain formability during production of the template. The template is in an initial stage produced with the aid of a shell and carbon fibre wires arranged in the latter. Matrix material is injected into the shell (tube). In connection with the application to the jawbone model, through-holes must be able to be arranged in the bridge material so that guide sleeves can be applied in the holes thus formed and constitute guide members for the hole-forming elements.

BACKGROUND OF THE INVENTION

The assembly template can also be shaped so that it bears on the gum where in some cases it can be in contact with the jaw bone via horizontally lying pins which touch the top of the jaw bone or dental crest. The invention also relates to the anchoring of such an assembly template.

Reference is made, inter alia, to Swedish Patent 457,691 which describes the production of oral and extra-oral prosthetic constructions made of composite material with a considerable fibre content.

Reference is also made to the Swedish patent application filed by the same Applicant and relating to a device or arrangement for applying sleeves in holes in connection with, inter alia, assembly templates for dental bridges or other tooth replacement fittings. The title of the application is "Device for forming holes and inserting sleeves in a unit incorporated in a dental attachment part".

SUMMARY OF THE INVENTION

In connection with the production of the assembly template in question or another auxiliary device of this type, it is expedient to keep the parts of the template or the like in a well-fixed spatial position in relation to an actual fixture or fixture dummy. In the position-determining function, there must be great precision both as regards the vertical position and the lateral displacement position in relation to the fixture or the dummy. In one embodiment, the sleeve or the like in question must assume a position above the fixture or the fixture dummy, which position can be concentric in relation to the longitudinal axis of the fixture or of the fixture dummy. The precision of said position or positions must prevail because the template, after its production on the jaw-bone model, must be able to be transferred to the patient and there assume a position in the patient's jaw bone which very accurately corresponds to the position which was present on the jaw-bone model. The invention aims to solve this problem among others.

With the assembly template material whose position has thus been determined in or on the jaw model, the assembly template must be able to be acted upon for changing shape or for material additions which means that the template is given support members which can cooperate with an upper surface of the jaw-bone model, which upper surface corresponds to the surface of the patient's jaw bone. The support members must be able to be given shapes and positions which, after removal of the position-determining members, allow the assembly template to maintain its precise position on the surface of the jaw bone model, and, upon transfer to the patient's jaw bone, the assembly template will be able, with the aid of the support members, to maintain a corresponding position which it assumes on the jawbone model. The irregularities in the surface of the jaw-bone model and in the patient's jaw bone in this case serve to obtain the position determinations in the transverse directions, and by means of the height-determining function the assembly template will be able to permit holes to be formed for fixtures in the patient's jaw bone in a position which very accurately corresponds to the position in or on the model. The accuracy can in this case be of the order of 0.05 mm. The invention solves this problem too. The invention solves this problem too.

The positional determination or fixing of the assembly template in question, with associated sleeves, to or on the jaw bone model must also be such that, when the template or template parts are screwed into or onto the jaw-bone model, it is not possible for the template or template parts, during the screwing or tightening, to permit changes in the position of the sleeves, which must not be allowed to tilt or otherwise change their positions in relation to the fixture dummy or fixture dummies during the tightening. The invention solves this problem too.

The feature which can principally be regarded as characterizing a device according to the invention is that a first member, for example in the form of an expansion spacer, cooperates both with the anchoring part or structural part, i.e. in the illustrative embodiment with the fixture or fixture dummy, and also with the element/sleeve, and in that a second member, for example an expansion screw, is designed in such a way that, when acted upon, it in turn acts upon the first member/expansion spacer so that the latter determines the position of the element/sleeve.

Embodiments of the invention are set out herein. Thus, for example, the device can include an expansion spacer which is acted upon by the expansion screw such that outer surfaces of the expansion spacer which cooperate with opposite surfaces on the respective sleeve are displaced radially outward and, upon cooperation, assume a parallelism with the inner surface of the sleeve with a high level of accuracy.

By means of what is proposed above, a position-determining device is obtained which secures the assembly template in place without risks of the assembly template tilting or changing position on account of the tightening in the actual fixture dummy or fixture. In the position thus assumed with the device, the assembly template can thus be assigned supporting or cooperating parts via which the assembly template cooperates with the jaw-bone model in order to obtain, with a high degree of accuracy, a precise position of the surface in question. The device also has a comparatively technically simple construction and can, for example, work with an external cone on an expansion screw and an internal cone on the expansion surface so that the parallelism between the cooperating surfaces on the expansion spacer and the sleeve in the dental bridge is present and is maintained during the subsequent work on the dental bridge.

BRIEF DESCRIPTION OF THE DRAWINGS

A presently proposed embodiment of a device having the features characterizing the invention will be described below with reference to the attached drawings, in which:

FIG. 1 shows, in a vertical view and partial cutaway view, a position-determining device for an assembly template in a fixture dummy in or on a jaw bone model, FIG. 2 shows, in a horizontal view, parts of the jaw bone model and an assembly template extending thereon, FIG. 3 shows, in a vertical view and partial cutaway view, an expansion spacer included in the device, FIG. 4 shows, in a vertical view, an expansion screw which can cooperate with the expansion spacer according to FIG. 3, FIG. 5 shows, in a side view, an embodiment of a sleeve fitted in the bridge, and FIG. 6 shows, in a horizontal view, the sleeve according to FIG. 5.

DETAILED DESCRIPTION OF EMBODIMENTS OF THE INVENTION

FIG. 1 shows a jaw-bone model labeled 1. The jawbone model represents a jaw bone of a patient. The model can be produced on different principles and thus, in one embodiment, the jaw model can be produced using stereolithography equipment known per se. An assembly template 2 is applied to the top surface 1a of the model. The assembly template is provided with a number of through-holes, of which one hole 3 is shown in the figure. The hole is obtained with the aid of a sleeve 4 which will constitute a guide member for a hole-forming member 5 shown diagrammatically or symbolically in connection with the template. The sleeve can be made of metal (titanium) or alloy. The template is secured in fixture dummies, of which one fixture dummy has been shown by 6 in FIG. 1. The fixture dummy can be of a type known per se and available on the open market, for example from Nobel Biocare AB. The assembly template can consist of a shell 2a which includes carbon fibre reinforcements 2b in a manner known per se. In addition, the shell contains matrix material 2c, for example acrylic plastic, which is injected inside the shell 2a. The template has been or is to be polymerized such that the template assumes a hardened form. The template is provided with cooperating members 2d and 2e which cooperate with the surface 1a on the jaw-bone model. The bottom surfaces 2d' and 2e' of the cooperating parts follow the contour of the top surface 1a with great precision so that the irregularities in the top surface 1a can be made use of as fixing or position-determining members when the template in the finished state is transferred to the patient's jaw bone. In or during the template production stage in which said cooperating members are established, it is important that the template can assume and maintain an exact position in relation to the fixture. According to the invention, this is achieved with the aid of position-determining members which include an expansion spacer 7 and an expansion screw 8. In the application procedure, the expansion spacer is pushed down through the recess 4a of the sleeve when the expansion spacer assumes a circumferential dimension which allows the spacer to be pushed down from above, cf. arrow 9, through the sleeve to make contact with the upper end 6a of the fixture dummy. The expansion spacer thus bears with its lower parts 7a against the upper parts 6a of the fixture dummy. The cooperating surfaces between the spacer and the dummy can be designed in a manner known per se, giving the spacer a distinct transverse position in relation to the fixture dummy. The pushing-down of the spacer in the sleeve is thus of an order of magnitude which means that two outwardly projecting flanges 7b and 7c on the upper parts 7d of the spacer can engage around the sleeve when the spacer is expanded radially outward at a stage after insertion. In the thus inserted position, the expansion screw 8 is applied from above, cf. arrow 9. The expansion screw is provided with a thread, in the present case an external thread 8a, by means of which the screw can be screwed down in a corresponding internal thread 6b in the fixture dummy. In the present illustrative embodiment, the expansion spacer and the expansion screw can be pushed down at the same time through the recess 4a, i.e. the expansion screw assumes a preliminary position in the expansion spacer. The expansion spacer can in this case be provided with an internal flange 7f which prevents the expansion screw from separating from the expansion spacer upon handling. The expansion screw has an external cone-shaped part 8b, and the expansion spacer has an internal cone-shaped part 7e. The cone-shaped parts cooperate with one another when the expansion screw is imparted rotational movements 10 relative to the spacer and is screwed down in the thread 0.6b. The cooperation between the cone-shaped parts means that portions 7d' of the upper parts of the expansion spacer are pressed radially outward, cf. radius R. The radial outward pressing ensures that outer surfaces 7d" are pressed so as to bear against the inner wall 4a of the sleeve 4 so that the template is fixed or its position determined in relation to the fixture dummy. The radial outward pressing and internal clamping which are effected with the aid of the expansion spacer and the expansion screw mean that no tilting movements occur, for example the tilting movements indicated by broken-line arrows 11, 12. The common longitudinal axis of the fixture dummy and of the spacer and of the screw is indicated by 13. The determination of position achieved in accordance with the above means that the spacer and screw 7 and 8, respectively, can adopt the common longitudinal axis with great accuracy.

With the assembly template in the position thus accurately fixed in relation to the top surface 1a of the jaw-bone model, the final shape can thus be given to the assembly template.

In FIG. 2, reference number 14 indicates a patient's upper jaw bone as seen from underneath.

The bridge 2 according to FIG. 1 has been transferred to the jaw and bears against its surface 14a with great accuracy by means of cooperating parts 2d and 2e which can be provided in a large number along the extent of the template 2 in the horizontal direction. The irregularities in the surface 14a can thus be used to fix the template in the transverse directions 15 and 16 relative to the jaw-bone surface 14a. In FIG. 2, three sleeves arranged along the longitudinal extent of the template are indicated by 4', 4" and 4'". The cooperating parts can be made of silicone material in conjunction with or after the production of the template.

FIG. 3 shows a detailed embodiment of an expansion spacer according to FIG. 1. The expansion spacer defines, with its vertical dimension H, the position of the sleeve 4 above the dummy 6 (see FIG. 1). In its upper half (related to FIG. 3), the spacer has one or more slits which extend in the longitudinal direction of the spacer. In the preferred illustrative embodiment, there are two such slits 7g. The slits extend at least along the outer surfaces 7d" which cooperate with the inner surface 4a of the sleeve 4 (see FIG. 1). In a preferred embodiment, the slit or slits 7g extend along at least half or more than half of the length of the expansion spacer. The slit arrangement and the inner recess 7h for the expansion screw and the transitions between the inner wall of the recess and the internal cone-shaped part 7e are thus such that, when the expansion spacer is acted upon by the expansion screw via the cone-shaped parts 7e and 8b (see FIG. 1), there is a substantially parallel displacement radially outward from the position shown in FIG. 3. In connection with the parallel displacement, the side parts 7i assume the position 7d''' where the parallel cooperation takes place with the inner surface 4a of the sleeve (see FIG. 1). In one embodiment, the side surfaces 7d" can be nonparallel with the inner surface 4a from the outset. In the radial displacement to the position 7d''', the surfaces 7d" assume their parallel positions with 4a so that clamping from inside is obtained along the entire inner surface 4a. The spacer also has an outer portion 7a' which can be of a type known per se in accordance with the above, which portion cooperates with the corresponding top side of the fixture dummy known per se. The portion 7a' can have or include a guide flange which cooperates with a corresponding guide flange on the fixture dummy in order to maintain the precise position in relation to the fixture in the vertical and transverse directions. The arrangement thus prevents the spacer from sloping in relation to the fixture dummy during and after tightening of the fixture dummy. Upon outward parallel displacements, the flanges 7b and 7c in accordance with the above come to engage around the end surfaces of the sleeve so that vertical fixing is obtained. The inwardly projecting flange 7f is also arranged such that it permits the insertion of the threaded part of the expansion screw. The cone-shaped part 7e can have a half cone angle α of 15°, for example.

In FIG. 4, a screwdriver slot is indicated by 8c and half the cone angle for the outer cone-shaped part 8b by β. The angle β can have a size corresponding substantially to the size of the internal cone 7e in the spacer, i.e. in the present case 15°. The external thread 8a is also indicated in FIG. 4.

FIGS. 5 and 6 show the extent of the inner surface 4a in the sleeve 4. In addition, the surfaces 4b and 4c are shown which can cooperate with the outwardly projecting flanges 7b and 7c (see FIG. 3) on the expansion spacer. The external surface 4d of the sleeve is provided with a small recess in order to ensure a good anchoring to the material of the assembly template in connection with the application of the sleeve in the template.

The invention is not limited to the embodiment described above by way of example, and instead it can be modified within the scope of the attached patent claims and the inventive concept.

The invention claimed is:

1. An arrangement for determining position and fixation of an element in a vertical direction and a transverse direction in relation to a part in or on a bone or a model of a bone, the arrangement comprising:
   a sleeve comprising an inner surface;
   an expansion spacer extending through the sleeve and comprising an outer sleeve engaging surface and an inner conical expansion surface, the expansion spacer comprising a first flange at a first end of the expansion spacer extending in a radial direction relative to a longitudinal axis of the expansion spacer and configured to engage a first end of the sleeve, the expansion spacer further comprising a second flange at a second end of the expansion spacer extending in the radial direction relative to the longitudinal axis of the expansion spacer and configured to engage a second end of the sleeve when the expansion spacer is expanded to vertically fix the expansion spacer with respect to the sleeve;
   an expansion screw extending through the expansion spacer and comprising an outer conical expansion surface configured to cooperate with the inner conical expansion surface on the expansion spacer to radially expand the expansion spacer causing the outer sleeve engaging surface on the expansion spacer to engage the inner surface of the sleeve, thereby determining the position of the sleeve relative to the part and fixing the sleeve, wherein radial expansion of the expansion spacer causes an outer surface of the expansion spacer to be positioned substantially parallel to the inner surface of the sleeve; and
   an assembly template configured to be arranged on soft tissue over the bone, the assembly template comprising a through hole extending therethrough, wherein the sleeve is arranged in the through hole,
   wherein when the expansion spacer is not expanded, the first flange has a first maximum diameter and the second flange has a second maximum diameter, the first maximum diameter being larger than the second maximum diameter and larger than a minimum diameter of the sleeve, the second flange being smaller than the minimum diameter of the sleeve, and when the expansion spacer is expanded, the second flange has a diameter being larger than the minimum diameter of the sleeve.

2. The arrangement according to claim 1, further comprising:
   an anchoring part or structural part comprising an inner threaded passage configured to cooperate with the expansion screw, wherein the expansion screw engages the threaded inner passage such that as the expansion screw is screwed into the anchoring part or structural part the expansion surface on the expansion screw engages the expansion surface of the expansion spacer.

3. The arrangement according to claim 2, wherein the anchoring part or structural part comprises a fixture or fixture dummy.

4. The arrangement according to claim 2, wherein the expansion spacer comprises a lower part having an end surface configured to bear against an upper part of the anchoring part or structural part.

5. The arrangement according to claim 2, wherein the expansion screw comprises a thread extending through the inner threaded passage of the anchoring or structural part, the thread of the expansion screw being configured to engage a thread of the anchoring part or structural part.

6. The arrangement according to claim 5, wherein the outer conical surface of the expansion screw is located between the thread of the expansion screw and an end surface of the expansion screw.

7. The arrangement according to claim 1, wherein the arrangement determines position and fixation of the sleeve in a vertical direction in relation to the part and in a transverse direction in relation to a longitudinal axis of the part.

8. The arrangement according to claim 1, wherein the expansion spacer comprises one piece.

9. The arrangement according to claim 1, wherein the template is jaw bone shaped.

10. The arrangement according to claim 1, wherein the expansion spacer, when inserted in the sleeve and in a position or state when not acted upon, has a circumferential dimension that permits removal of the expansion spacer from the template via the sleeve, and wherein the expansion spacer determines a position of the sleeve in a position or state when acted upon by the expansion screw in which a circumferential increase is thus present and cooperation with the sleeve takes place.

11. The arrangement according to claim 1, wherein the expansion spacer, at parts cooperating with the sleeve, comprises at least two slits that extend in a longitudinal direction of the sleeve and in a wall of the sleeve continuously, which slits, together with a remaining portion of the expansion spacer, permit radially directed displacement, with retention or adoption of a substantial parallel positioning of outer surfaces of the expansion spacer which can cooperate with the inner surface of the sleeve.

12. The arrangement according to claim 1, wherein the template comprises carbon fiber-reinforced plastic and a surrounding shell, into which curable or hardenable means can be injected and can cure or harden in order to give the template a distinct and permanent shape.

13. The arrangement according to claim 1, wherein the template and the sleeve can be transferred to a patient's jaw bone which the model simulates, and wherein the sleeve and template then constitute guides for forming holes in the patient's jaw bone.

14. The arrangement according to claim 1, wherein the spacer comprises at least one slit extending through a wall of the spacer in a longitudinal direction of the spacer.

15. The arrangement according to claim 14, wherein the at least one slit extends at least along the sleeve engaging surface.

16. The arrangement according to claim 15, wherein the at least one slit extends from a top of the spacer along at least half of the length of the spacer.

17. The arrangement according to claim 1, wherein the expansion spacer comprises at least one slit extending through the spacer in the vicinity of the sleeve engaging surface.

18. The arrangement according to claim 17, wherein the slit extends through the first flange.

19. The arrangement according to claim 17, wherein the slit extends at least along the outer sleeve engaging surface.

20. The arrangement according to claim 1, wherein the first flange extends completely or partially over a first end surface of the sleeve, and the second flange extends completely or partially over a second end surface of the sleeve when the expansion spacer is radially expanded.

21. The arrangement according to claim 1, wherein the template comprises a plurality of through holes extending therethrough, wherein a plurality of sleeves are arranged in the through holes, a plurality of expansion spacers extend through the sleeves, a plurality of expansion screws extend through the expansion spacers and are secured to a plurality parts arranged in a model of a jaw bone to secure the template to the model of the jaw bone.

22. The arrangement according to claim 21, wherein the template further comprises support parts which cooperate with said sleeves so that the template, upon removal of the expansion screws and the expansion spacers, acquires a precise lateral displacement position in which the positions of the sleeves are well defined.

23. The arrangement according to claim 21, wherein the model has a desired shape on a side facing toward an outwardly directed surface of the model.

24. An arrangement for determining position and fixation of an element in a vertical direction and a transverse direction in relation to a part in or on a bone or a model of a bone, the arrangement comprising:

a sleeve comprising an inner surface;

an expansion spacer extending through the sleeve and comprising an outer sleeve engaging surface and an inner conical expansion surface, the expansion spacer comprising a first flange at a first end of the expansion spacer extending in a radial direction relative to a longitudinal axis of the expansion spacer and configured to engage a first end of the sleeve, the expansion spacer further comprising a second flange at a second end of the expansion spacer extending in the radial direction relative to the longitudinal axis of the expansion spacer and configured to engage a second end of the sleeve when the expansion spacer is expanded to vertically fix the expansion spacer with respect to the sleeve;

an expansion screw extending through the expansion spacer and comprising an outer conical expansion surface configured to cooperate with the inner conical expansion surface on the expansion spacer to radially expand the expansion spacer causing the outer sleeve engaging surface on the expansion spacer to engage the inner surface of the sleeve, thereby determining the position of the sleeve relative to the part and fixing the sleeve causing the expansion spacer to engage the sleeve, wherein radial expansion of the expansion spacer causes an outer surface of the expansion spacer to be positioned substantially parallel to the inner surface of the sleeve; and an assembly template configured to be arranged on soft tissue overlying the bone, the assembly template comprising a plurality of through holes extending therethrough, wherein the arrangement comprises a plurality of sleeves arranged in the through holes, a plurality of expansion spacers arranged in the plurality of sleeves and a plurality of expansion screws, and wherein the sleeves are arranged to lie opposite fixture dummies in a model or a fixture, wherein when the expansion spacer is not expanded, the first flange has a first maximum diameter and the second flange has a second maximum diameter, the first maximum diameter being larger than the second maximum diameter and larger than a minimum diameter of the sleeve, the second flange being smaller than the minimum diameter of the sleeve, and when the expansion spacer is expanded, the second flange has a diameter being larger than the minimum diameter of the sleeve.

25. A fixing component and a assembly template having a sleeve for positioning and fixing an element in a vertical direction and a transverse direction in relation to a part in or on a bone, on soft tissue overlying bone or a model of a bone, the fixing component comprising:

an expansion screw comprising a conical expansion surface, a first portion of the fixing component comprising an outer sleeve engaging surface engaging the sleeve arranged in a through hole in an assembly template, a central passage configured to receive the expansion screw, the central passage comprising an inner conical expansion surface configured to cooperate with the conical expansion surface on the expansion screw to radially expand the first portion causing the outer sleeve engaging surface on the first portion to engage the inner surface of the sleeve, thereby determining the position of the sleeve relative to the part and fixing the sleeve causing the first portion to engage the sleeve, a first flange at a first end of the first portion extending in a radial direction relative to a longitudinal axis of the first portion and configured to engage a first end of the sleeve; and a second flange at a second end of the first portion extending in the radial direction relative to the longitudinal axis of the first portion and configured to engage a second end of the sleeve when the first portion is expanded to vertically fix the first portion with respect to the sleeve, a second portion connected to the second end of the first portion and configured to cooperate with an anchoring element;

wherein the fixing component comprises at least one slit extending at least along the entire longitudinal length of the first portion and through the first and second flanges.

26. The fixing component according to claim 25, wherein the first flange extends completely or partially over a first end surface of the sleeve, and the second flange extends completely or partially over a second end surface of the sleeve when the first portion is radially expanded.

27. The fixing component according to claim 25, wherein the template comprises a plurality of through holes extending therethrough, wherein a plurality of sleeves are arranged in the through holes, a plurality of first portions extend through the sleeves, a plurality of expansion screws extend through the first portions and are secured to a plurality parts arranged in a model of a jaw bone to secure the template to the model of the jaw bone.

28. The fixing component of claim 25, wherein when the first portion is not expanded, the first flange has a first maximum diameter and the second flange has a second maximum diameter, the first maximum diameter being larger than the second maximum diameter.

29. The fixing component of claim 25, wherein when the first portion is expanded, the outer surface of the first portion is substantially parallel to the inner surface of the sleeve.

30. The fixing component of claim 29, wherein when the first portion is not expanded, the outer surface of the first portion is non-parallel to the inner surface of the sleeve.

* * * * *